US00PP37243P2

(12) United States Plant Patent
Hansen

(10) Patent No.: US PP37,243 P2
(45) Date of Patent: Feb. 3, 2026

(54) ***NEPETA* PLANT NAMED 'Lemon Purrfection'**

(50) Latin Name: ***Nepeta* hybrid**
Varietal Denomination: Lemon Purrfection

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,619

(22) Filed: Jun. 13, 2025

(51) Int. Cl.
*A01H 5/02* (2018.01)
*A01H 6/50* (2018.01)

(52) U.S. Cl.
USPC ..... Plt./263.1

(58) Field of Classification Search
USPC ..... Plt./263.1
CPC ... A01H 5/12; A01H 5/02; A01H 5/00; A01H 6/50
See application file for complete search history.

(56) References Cited

U.S. PATENT DOCUMENTS

PP35,867 P2 * 6/2024 Hansen ..... Plt./263.1

* cited by examiner

*Primary Examiner* — June Hwu

(57) ABSTRACT

The new and distinct hardy perennial *Nepeta* plant named 'Lemon Purrfection' has a dense, compressed mound, with compact habit and arching to horizontal stems. The new plant begins flowers in late spring and continues and repeats until autumn frost without deadheading. The flowers are bluish-lavender with purple spots and persistent mauve calyces just above the complementing bright chartreuse-yellow, cordate, fragrant foliage. The new plant is useful in the landscape en masse, as an accent, or in containers to bring color and fragrance to a garden and attract butterflies and hummingbirds.

1 Drawing Sheet

Botanical denomination: *Nepeta* hybrid.
Variety designation: 'Lemon Purrfection'.

STATEMENT REGARDING PRIOR DISCLOSURES UNDER 37 CFR 1.77(B)(6)

The first offer for sale of 'Lemon Purrfection' was by Walters Gardens, Inc. on Jun. 17, 2024, followed on Feb. 1, 2025, by the posting of a brief description and photograph on a website operated by Walters Gardens, Inc., who obtained the plant and all information relating from the inventor. No plants of *Nepeta* 'Lemon Purrfection' have been sold or offered for sale in this country or anywhere in the world nor has any disclosure of the new plant been made more than one year prior to the filing date of this application, and such sale or disclosure within one year was either derived directly or indirectly from the inventor is therefore a 35 U.S.C. § 102(b) exception.

BACKGROUND AND ORIGIN OF THE PLANT

The present invention relates to a new and distinct cultivar of *Nepeta* named 'Lemon Purrfection'. The new plant was selected as a single seedling from the progeny of a self-pollination of the proprietary unreleased hybrid known only as NEP-2019-tet-1 (not patented). The pollination was directed by the inventor in the summer of 2021. The seed was harvested later in the summer of 2021, grown out, evaluated in subsequent years, and a single seedling was selected and assigned the breeder code 21-2-1 for the trial period prior to naming. 'Lemon Punfection' was approved in a final evaluation in the summer of 2023 and slated for later introduction. The new plant was selected based on compact habit, flower cover, foliage color, and early and long blooming season. The new plant has been asexually propagated at a wholesale nursery in Zeeland, Michigan first by division in the late summer of 2022 followed by tip cuttings with the resultant plants remaining identical to the original plant, stable and true to type in successive generations.

The parent plant has leaves that are more chartreuse and less yellowish, flowers of light lavender, and more open habit and less dense habit.

SUMMARY OF THE INVENTION

*Nepeta* 'Lemon Purrfection' is different from its parents and all other Catmint cultivars known to the inventor. The nearest comparison plants known to the inventor include: 'Cat's Pajamas' U.S. Plant Pat. No. 31,127, 'Chartreuse on the Loose' U.S. Plant Pat. No. 35,867, 'Kitten Around' U.S. Plant Pat. No. 30,940, 'Limelight' (not patented), and 'Purrsian Blue' U.S. Plant Pat. No. 24,788.

'Cat's Pajamas' has a more upright rounded habit and has foliage that is a deeper green and flower coverage from the top to bottom of the stem. 'Chartreuse on the Loose' has a more open and horizontal habit. 'Kitten Around' has a smaller rounded habit and the foliage is deeper green. 'Limelight' has a shorter and broader habit, the foliage is smaller and less yellowish, and flowers for a shorter period. 'Purrsian Blue' has a larger habit, smaller more purplish-blue flowers, and the foliage is deeper green.

The present invention has not been evaluated under all possible environmental conditions. The phenotype may vary with changes in the environment such as light, temperature, water, nutrient availability, etc. without a change in the genotype of the plant. *Nepeta* 'Lemon Purrfection' is unique from all other Catmint known to the inventor in the following combined traits:

1. The habit is dense, rounded, compressed, and compact with arching to horizontal stems;
2. Foliage is cordate, small with crenate teeth, and has an herbal fragrance;
3. Leaf color is bright chartreuse-yellow;
4. Flowers are large, bluish-lavender with purple spots and persistent mauve-colored calyces just above the foliage;
5. Plant flowering starts in late spring and continues without deadheading until autumn frost.

BRIEF DESCRIPTION OF THE DRAWINGS

The photographs of the new plant *Nepeta* 'Lemon Purrfection' are of a two-year old plant in a full-sun, trial garden at a wholesale perennial nursery in Zeeland, Michigan and demonstrate the unique aspects of the new plant. The colors are as accurate as reasonably possible with color reproductions. Ambient light spectrum, temperature, source, and direction may cause the appearance of minor variations in color.

DETAILED PLANT DESCRIPTION

Figure 1:
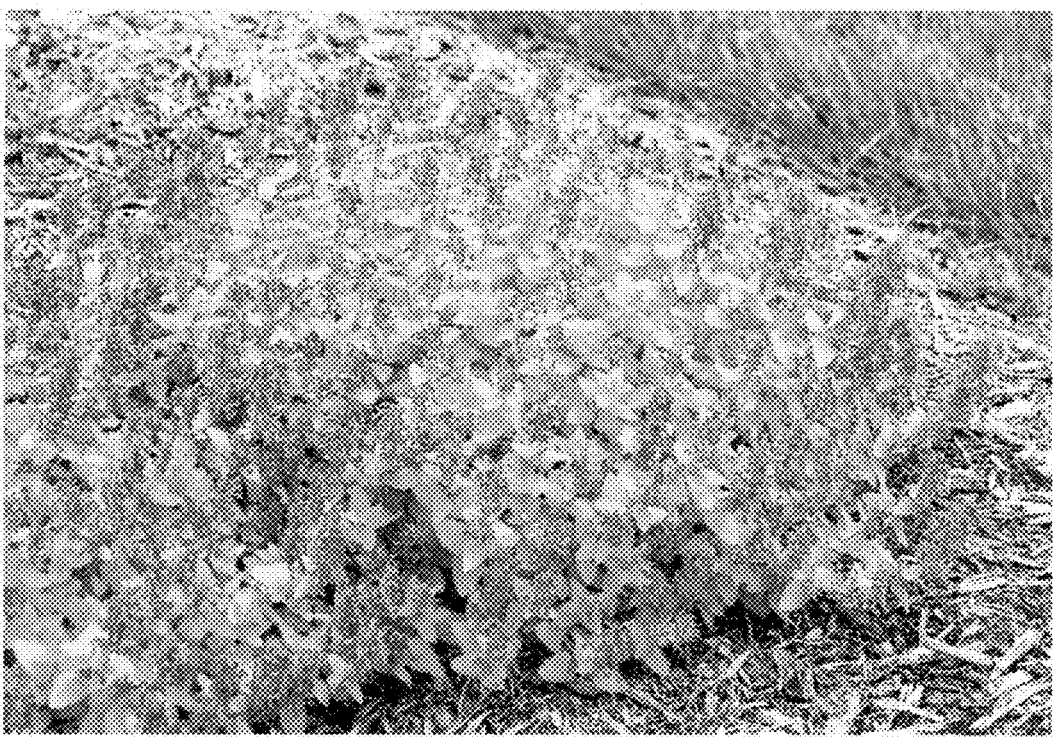
FIG. 1 shows the overall habit of the new plant.
Figure 2:
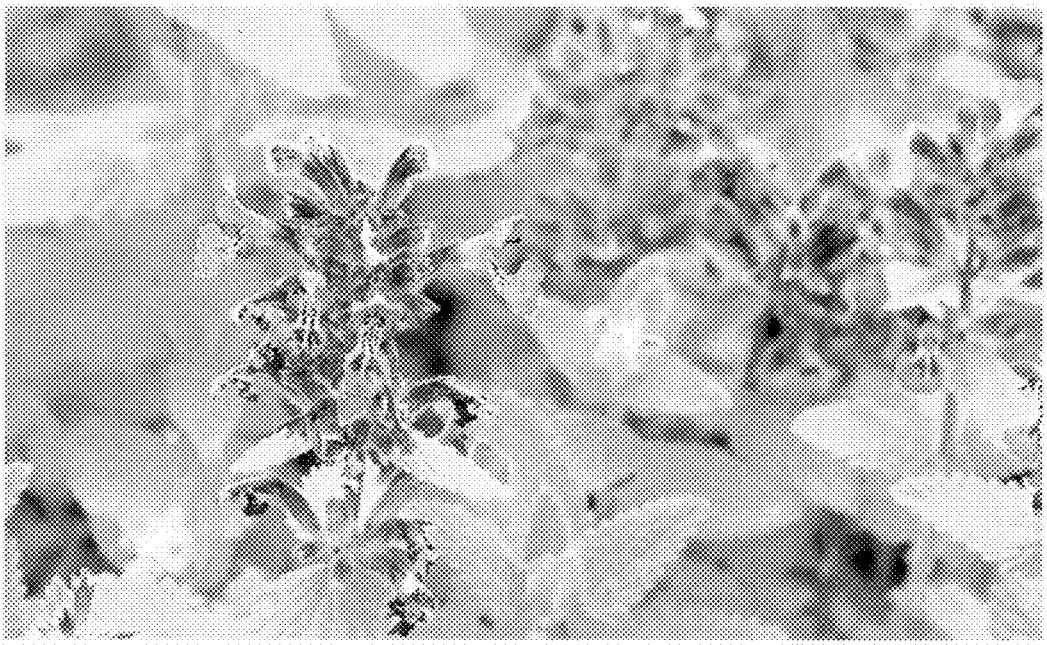
FIG. 2 shows a close-up of the flowers, buds, and stems.

The following descriptions are based on a two-year-old plant of *Nepeta* 'Lemon Purrfection' grown in a partially-shaded greenhouse and a full-sun trial garden in sandy loam soil with supplemental water and fertilizer as needed. The color references are based on the 2015 edition of The Royal Horticultural Society Colour Chart except where common dictionary terms are used. The new plant has not been observed under all possible environments. The phenotype may vary slightly with different environmental conditions, such as temperature, light, fertility, moisture, and maturity levels, but without any change in the genotype.

Parentage: The parent is the proprietary hybrid NEP-2019-tet-1;

Plant habit: Herbaceous perennial; multi-stemmed, foliage mounding to about 20 cm tall and 58 cm wide at the base and 29 cm tall in flower;

Growth: Rapid; time to initiate roots at 23° C. about one week; finishing in a standard #1-15 cm container in about 8 to 10 weeks from rooted 25 mm plug;

Root: Fine, freely branching; color between RHS NN155C and RHS 158D depending on soil type and nutrient content;

Foliage: Opposite; simple; cordate; rugose on both abaxial and adaxial surfaces; margins crenate with about 13 teeth per side; micro-puberulent on adaxial and abaxial surfaces; apex acute; base cordate; blade size to about 52 mm long and 35 mm wide near base, average about 45 mm long and 30 mm across; teeth to about 4.5 mm wide and 2.5 mm long;

Foliage fragrance: Foliage and stem with herbal fragrance;

Leaf color: Variable; young expanding adaxial a blend between RHS 144A and RHS 145A and nearest RHS 145A, young expanding abaxial in sun garden a blend between RHS 146D and RHS 145A and nearest RHS 145A; mature adaxial variable, nearest RHS 150D, nearest RHS 145A, and as bright as nearest RHS 11D, mature abaxial between RHS 146D and RHS 147C; greenhouse grown young adaxial between RHS 144C and RHS 146D, young abaxial between RHS 146D and RHS 145B; greenhouse grown mature adaxial between RHS N144D and RHS 146D, mature abaxial between RHS 145A and RHS 147C;

Venation: Reticulate; impressed on adaxial surface and costate on abaxial surface;

Vein color: Greenhouse grown adaxial nearest RHS 143A, abaxial midrib and proximal primary veins nearest RHS 145D, distal veins nearest RHS 146C; full-sun garden grown adaxial nearest RHS 146D, abaxial between RHS 148C and RHS 148D;

Petiole: Micro-puberulent adaxial and abaxial; slightly concavo-convex; to about 23 mm long and 1.5 mm across at base; average about 12 mm long and about 1.5 mm across;

Petiole color: Adaxial nearest and RHS 145C, abaxial between RHS 145D and RHS 145C;

Stem: Micro-puberulent; quadrangular; arching to horizontal; heavily branched; about 39 cm long before flowers and 2.5 mm across at base; about 80 stems per plant; with compound branches in proximal nodes; about 6 to 8 branches per stem, branches to about 10 cm long and 2 mm across at base;

Stem color: Lower portion nearest and RHS 145C, with the upper portion in heavy sun exposure having light to moderate blush of nearest RHS 183B;

Nodes: Average about 3 cm apart with the greatest distance in the middle of the stem; about 10 nodes per stem before flowers;

Node color: Same as surrounding stem;

Inflorescence: Cymosely clustered with many flowers typically branched at verticillasters in the distal 8 to 10 nodes; about 10 to 34 flowers per node and about 100 to 200 flowers per inflorescence stem or peduncle;

Peduncle: Quadrangular; micro-puberulent; flowering portion arcuate upwardly; flowers on single verticillaster flowering over a prolonged period; flower portion in distal 12 cm and 4.5 cm wide;

Peduncle color: Nearest RHS 146C proximally and distally nearest RHS 146B with a strong blush of RHS 183C;

Pedicel: Sessile to 3 mm long and 0.3 mm diameter; micro-puberulent; cylindrical; aspect upwardly;

Pedicel color: When present between RHS 146D and RHS 145C with a variable blush to solid of nearest RHS 183D;

Flower bud: Arcuate clavate; about 11 mm long, 4 mm tall, 3 mm wide in bulb portion, and 1.7 mm diameter at base; abaxial petal and calyx surfaces glandular to puberulent;

Flower bud color: Greenhouse color-petal portion nearest RHS 91C with petal margins between RHS 93B and RHS 94A, calyx proximal portion between RHS 138C and RHS 145C and distally nearest RHS 138B; full-sun-petal portion between RHS 86B and RHS 90B with calyx nearest RHS N79B distally on dorsal side and veins extending proximally with ventral side and proximal between veins between RHS 145D and RHS 145C;

Flowers: Zygomorphic; perfect; bilabiate; sympetalous with basal 10 mm fused; lips opening to form about a 60 to 80-degree angle to each other; 14 mm long and 11 mm tall and 8 mm wide; in dense verticillasters;

*Upper lip.*—With two lobes; puberulent on abaxial surface, glabrous adaxial; lobes about 2 mm long and 4 mm wide above fusion with lower lobe and separated with other upper lobe in the distal 2 mm; lobes with rounded apex; total size of lip about 14 mm long and about 2 mm wide at fusion.

*Lower lip*.—Consisting of three lobes; adaxial glabrous, abaxial puberulent proximally and glabrous distally; center and largest lobe highly concave with rounded apex and crenate margin having five indentations about 1 mm deep in center and the four lateral incisions to about 0.5 mm deep, overall about 6 mm wide near apex and 5 mm long; two side lobes with rounded apices and entire margin; center lobe to about 10 mm long in total, 8 mm long from fusion, and up to 9 mm across when flattened; side lobes 2 mm long from fusion and 4 mm across; micro-puberulent abaxial and glabrous near margin, glabrous adaxial.

*Young petal color*.—Upper lip adaxial free portion nearest RHS N87B and abaxial portion between RHS N87B and N87C; lower lip adaxial proximally nearest RHS N87C toward the edges and in the longitudinal center nearest RHS NN155D, distally nearest RHS N88B, maculate with spots about 0.2 mm diameter proximally to distally about 1 mm diameter and sometimes fused of nearest 86A, abaxial nearest RHS N88B toward edges and nearest RHS 85D in longitudinal center with spots in the proximal half about 0.2 mm diameter of nearest RHS 86C.

*Mature petal color*.—With no significant color change.

*Corolla tube color*.—Adaxial and abaxial proximal 5 mm nearest RHS NN155D, distal 5 mm adaxial nearest RHS 85D with spots on lower lip portion of nearest RHS 86C, distal 5 mm abaxial nearest RHS N88D.

Calyx: Gamosepalous; 5-merous fused into a tube in basal 6 mm; to 8 mm long, 3 mm tall, and 2 mm across at apex;

Sepals: Five; acute apex; basal 6 mm fused, free in distal 2 mm; margin micro-ciliolate; with about 3 conspicuous longitudinal veins; glabrous adaxial, micro-pubescent abaxial; persistent after flower abscission;

Sepal color: Adaxial nearest RHS 144D with veins nearest RHS 146A and faint blush of nearest RHS N79B; abaxial proximal 3 mm nearest RHS 138C, distal portion nearest RHS 146D with a heavy blush on the dorsal side of nearest RHS 86B and veins nearest RHS 146B;

Gynoecium: Single compound ovary with two carpels, about 14 mm long;

*Style*.—About 12 mm long and 0.3 mm diameter; color proximally between RHS 84D and RHS NN155D with distal 2 mm nearest RHS N87D.

*Stigma*.—Bifurcate in distal 1 mm and about 0.1 mm diameter; with sharply acute apex; color nearest RHS 86A.

*Ovary*.—Four-lobed, each lobe ovoid, about 0.5 mm long and 0.2 mm across; color nearest RHS 146D.

Androecium: Four;

*Filaments*.—Cylindrical; straight; in two sets of two; longer set to 12 mm long and 0.3 mm diameter, adnate to petals in basal 8 mm, free in distal 4 mm; shorter set to 10 mm long and 0.3 mm diameter, adnate in basal 7 mm, free in distal 3 mm; color proximally nearest RHS NN155D and distally nearest RHS 85A.

*Anthers*.—Oblong ellipsoidal; about 1.2 mm long and 0.5 mm across; color nearest RHS N92C.

*Pollen*.—Abundant; color nearest RHS NN155B.

Flowering period: In Western Michigan beginning in late spring and continuing and repeating until fall frost without deadheading; individual flowers remain open for about three days;

Flower fragrance: None detected;

Flower attitude: Outwardly to slightly upwardly;

Fruit and seed: Prolific; nutlets; flattened ellipsoid; about 1.5 mm long, 1 mm across, and 0.5 mm thick; nearest RHS 200A;

Pest and disease susceptibility: Typically, not prone to browsing by Odocoileus or Sylvilagus but no resistance beyond that which is typical for *Nepeta*.

Growth: The new plant grows well with low to average soil moisture, in full sun to part shade, and is winter hardy in USDA zones 3 through 8.

I claim:

1. A new and distinct hardy perennial *Nepeta* plant named 'Lemon Purrfection' essentially as herein described and illustrated.

* * * * *